United States Patent [19]
Lemelson

[11] Patent Number: 5,735,276
[45] Date of Patent: Apr. 7, 1998

[54] METHOD AND APPARATUS FOR SCANNING AND EVALUATING MATTER

[76] Inventor: Jerome Lemelson, 868 Tyner Way, Incline Village, Nev. 89450

[21] Appl. No.: 407,690

[22] Filed: Mar. 21, 1995

[51] Int. Cl.[6] .............................. A61B 5/00; G01N 21/64
[52] U.S. Cl. ........................ 128/653.1; 356/346; 378/45; 128/665; 250/458.1
[58] Field of Search .................. 128/653.1, 664, 128/665, 633; 606/2, 10–12; 356/346; 250/458.1, 461.1, 461.2; 378/44, 45, 62, 64, 65; 348/68, 77, 164

[56] References Cited

U.S. PATENT DOCUMENTS

| | | |
|---|---|---|
| 2,584,052 | 1/1952 | Sandorff et al. . |
| 2,661,902 | 12/1953 | Wolff et al. . |
| 2,789,765 | 4/1957 | Gillings . |
| 4,758,727 | 7/1988 | Tomei et al. . |
| 4,973,848 | 11/1990 | Kolobanov et al. . |
| 5,091,652 | 2/1992 | Mathies et al. . |
| 5,283,433 | 2/1994 | Tsien . |
| 5,284,149 | 2/1994 | Dhadwal et al. . |
| 5,408,996 | 4/1995 | Salb . |
| 5,418,371 | 5/1995 | Ausland et al. . |
| 5,421,337 | 6/1995 | Richards-Kortum et al. . |
| 5,424,959 | 6/1995 | Reyes et al. . |
| 5,456,252 | 10/1995 | Vari et al. . |
| 5,464,013 | 11/1995 | Lemelson . |
| 5,562,100 | 10/1996 | Kittrell et al. . |

OTHER PUBLICATIONS

A Microfluorometric Scanning . . . Cells, R.C. Mellors et al.
A Microflurometric Scanner . . . Cytology, R.C. Mellors et al.
The Cytoanalyzer— An Example of . . . Research, W.E. Tolles.
Journal of Scientific Instruments, vol. 32, May 1995.
Kurze Mitteilungen – Brief Reports.
Programming A Digital Computer . . . W. Welkowitz.
The Automatic Counting . . . Cells, Cooke–Yarborough et al.
Automatic Counting . . . Particles, W.H. Walton.
Television in Medicine . . . Biology, V. K. Zworykin et al.
On the Theory of Counting . . . Apparatus, Lagergrantz.

Primary Examiner—Marvin M. Lateef
Assistant Examiner—Shawna J. Shaw
Attorney, Agent, or Firm—Louis Weinstein

[57] ABSTRACT

A system and method for analyzing matter by computer analysis of electrical signals generated by sensing radiation reflected from matter (i.e. tissue, cells, liquid, gaseous or solid particles in a liquid or gas) and/or generated due to fluorescence. In one embodiment, a short pulse of laser radiation is directed at matter also scanned by an electro-optical scanning means to generate image signals. Fluorescent radiation and reflected radiation generating image signals, generate respective variable electrical signals which are computer processed and analyzed to detect and determine the chemical and/or biological composition of the matter. A television camera scans the matter and generates video signals for computer processing and analysis. Simultaneously or sequentially, pulsed laser energy is directed against plural locations of scanned matter, wherein each of such pulses generates a short duration of fluorescent energy in different select portions of the matter under analysis. Fluorescing light is photoelectrically detected generating variable electrical signals for each portion of fluorescing matter, which signals are computer processed and analyzed along with signals output by the television camera to provide information used to intelligibly indicate: (a) composition of such matter, (b) presence of one or more chemical and/or biological agents in such matter, (c) whether the matter is defective or diseased or, (d) a combination of such indications. The liquid may be any body fluid. Manipulators are provided to move the TV camera, lasers, sensors and treatment lasers and/or surgical instruments.

83 Claims, 5 Drawing Sheets

METHOD AND APPARATUS FOR SCANNING AND EVALUATING MATTER

FIELD OF THE INVENTION

The present invention relates to method and apparatus for analyzing and/or treating matter and more particularly to method and apparatus for such analysis and treatment employing automated computer and laser scanning techniques.

SUMMARY OF THE INVENTION

This invention relates to a system, method and apparatus for detecting and quantizing disease, such as cancer, employing radiation, such a laser radiation, which is directed as a beam or beams to a select portion of the skin or internal tissue of a patient such as via a catheter or instrument, which select portion includes diseased tissue such as cancerous or precancerous cells against or across which the radiation beam is scanned. The radiation beam is so generated and varied during its scanning movement across select tissue and/or as it statically intersects select tissue such as a tumor or a malignancy, that it causes variable fluorescence or spectral radiation to be emitted by the select tissue, cancer or precancerous cells. Photoelectric or optical detection of such spectral radiation results in the generation of variable electrical or optical signals which are computer processed and analyzed in a manner to (a) detect the presence of the disease or cancer and/or precancerous cells, (b) quantize the cancer and/or precancerous cells in terms of their number, distribution and/or the shape and location of the malignancy, (c) determine the type of cancer, (d) determine the stage of the malignancy, and (e) determine the stages of different portions and/or cells of the malignancy or disease.

Forms and operational modes of the invention are noted as follows:

(a) In a first form of the invention, a laser beam is generated by a tunable laser and directed at a first intensity and frequency or wavelength against a select portion of skin. The laser is hand-held or held by a support adjacent to or within a patient. Such laser radiation may also be directed from a (solid state) laser at the end of an elongated part of an instrument such as a laparoscope, catheter or endoscope or along a light pipe defined by an elongated passageway in a tube or optical fiber(s) of such instrument from an external laser or a laser coupled to or defined by such fiber(s), against a select portion of internal tissue such as the wall of a body duct or a lesion or tumor (polyp) formed therein or in tissue adjacent said duct, or other type of diseased tissue from a laser within or external of such elongated part. The intensity and frequency of the first laser radiation is such as to cause all or a portion of the tissue or cells of the tissue or body fluid it irradiates to become excited and fluoresce at a select frequency or wavelength. Such fluorescent radiation (with or without the reflected radiation) is photoelectrically detected by one or more photoelectric cells or photodiodes located adjacent the laser or within the instrument. The resulting electrical or optical signals are computer processed and analyzed to generate first code signals which are modulated with or define first information relative to the cells or tissue so excited. Such first code signals are then employed to intelligibly indicate first information about the fluorescing tissue, such as if it is cancerous or precancerous.

In accordance with such first code signals and/or the program of the computer, control signals are next generated by the computer which are applied to controllably vary the frequency or wavelength and/or the intensity of the laser radiation while it is directed against the same tissue to excite same or cause it to vary the fluorescent or spectral radiation it emits. As such fluorescence radiation is generated and/or so varies when it attains a select frequency or wavelength, it is photoelectrically detected and the resulting signals output by the photoelectric detector are computer processed and analyzed to generate second code signals. The series of code signals so generated are computer analyzed to generate further code signals in one or more analyzing steps, which further code signals may be employed to intelligibly indicate one or more of the variables described above. Fuzzy logic, neural network and/or so-called expert computer subsystems may be employed to effect such analysis and the quantizing of the results.

(b) In a second method, the laser radiation beam described is caused to effect scanning movement with respect to select skin or internal tissue of a patient including at least a portion thereof which is cancerous and/or a precancerous portion. The scanning may be continuous along a select path or group of paths such as spiral or raster paths, and/or stepped from one tumor or tumor portion to the next, or the computer analysis may be effected while the beam is held stationary at one or a series of select locations such as at different small tumors in a select portion of tissue or organ of the patient. The above procedure, wherein the laser beam is continuously and/or intermittently varied in wavelength or frequency and/or in intensity under computer control, is employed while the beam is in scanning movement and/or while it is stopped at such plurality of select locations. The resulting code signals are computer analyzed to quantize the malignancy, tumor or tumors. The codes generated at each step and/or location of the beam may be employed by the computer to controllably vary the wavelength or frequency and intensity of the tunable scanning laser beam during a single scan or during repetitive scans of the same portion or portions of tissue (or body fluid such as blood, lymph fluid, etc.), again employing an expert system, fuzzy logic and/or neural network computer processing. The code signals per se or combined with timing code signals generated during scanning may be employed to locate and indicate the size and shape of the tumor or tumors scanned. Such computerized scanning and spectral analysis may be combined with image analysis techniques to either define, and/or quantize and locate the tumor(s) and determine the stage or stages of the cancer(s) detected and scanned.

(c) In a third computer controlled method, a plurality of lasers are employed to generate and simultaneously or sequentially direct respective laser light beams of different select wavelengths or frequencies (and/or intensities) at the same tissue while such radiation is stationary or in scanning movement. Computerized fluorescence radiation analysis and/or image analysis is effected as above to detect, locate, quantize and determine the state or stage of cancer of the tumor or tumors scanned or the disease under investigation.

(d) In a fourth method, one or more of the tissue scanning techniques set forth are employed to generate quantitative information in the disease or diseased tissue, such as the type of cancer, its stage of development, the size of a tumor or tumors, the location(s) thereof, etc. Such information is analyzed by one or more expert systems, fuzzy logic and/or neural network computers which generate coded control signals. The control signals are employed to control the operation(s) of one or more motors, solenoids, controls or the like for controlling and operating a treatment system, such as one which applies select amounts of one or more drugs and/or radiation (beams) operable to destroy or cure the disease such as destroy cancer or precancer cells or render same noncancerous.

This invention further relates to a system and method for scanning matter, such as chemical and/or biological matter in liquid or gaseous form or solid particles or matter carried in a liquid or gas, to automatically detect and quantize select matter therein. While a particular and preferred application of the invention is to automatically scan and detect select biological material or elements, such as microbes, viruses and select proteins, chemicals or biochemicals in a mixture of matter, such as body fluid including blood, lymph fluid, saliva, urine and/or other body fluid, the invention may also be employed to scan, detect and separate, selectively irradiate or destroy or otherwise change select biological elements in vivo or in vitro with respect to living animal or plant life, such as a living being, a culture or otherwise confined amount of biological material, a sample of tissue, a single cell sample or group of cells, bacteria, virus, protein or proteins or a mixture thereof which is desired to be biologically engineered, purified, genetically changed or selectively destroyed.

To the end of achieving such change, separation or detection of select matter in a sample, batch or flowing stream thereof, a beam or beams of select radiation such as generated by a laser, electron gun and/or other means, is either directed along a single axis and at a moving stream or a moving or stationary sample of matter or is caused to be deflected and thereby controllably scan a stationary quantity of matter or moving matter such as a fluid stream or quantity of matter supported by a moving substrate. The radiation beam is either collimated or narrow enough or focused in a manner to permit it to intersect and react on a domain of matter, such as a select organism, tissue specimen, single cell, bacteria, virus or otherwise formed small quantity of matter which is secured to or forms part of a substrate or is floating on or with a liquid such as blood or other fluid, plant fluid or the like. Thus, during relative scanning movement of the matter or liquid containing same, when the radiation beam intersects such select matter, it may cause a select amount of same or an ingredient therein to fluoresce and emit fluorescent energy of sufficient intensity to be photoelectrically detected by a photoelectric detection means, which is operable to receive such fluorescent energy during the scanning operation and convert same to an electrical signal modulated with information relating to the fluorescent energy received.

In a modified form of the invention, light reflected from a specimen is also photoelectrically detected during scanning and radiation variations therein caused by variations in the reflectivity of the matter scanned, cause corresponding modulations of the electrical signal or signals output by the photoelectric detection means. Such reflections and/or fluorescent-energy-generated detection signals are recorded and/or are computer processed and analyzed immediately and in real time by a computer which is operable to generate control or coded electrical signals which are employed thereafter to effect one or more automatic functions. One such function may comprise intelligibly indicating the presence of such select matter. Another function may comprise intelligibly indicating the location or locations of such select matter. A third function may comprise intelligibly indicating the quantity or density of such select matter in the sample or quantity of matter scanned. Another function may comprise intelligibly indicating the presence, quantity or density of a plurality of different types of select matter. Such functions may also be supplemented by the generation of information signals and may be computer processed and analyzed to effect automatic control of signal variable means for reacting on matter scanned, a select portion or portions thereof detected as a result of such scanning to controllably destroy, biologically change and/or separate same from the remaining matter scanned. Changes in, destruction of or separation of select portions of matter, such as select cells in blood or other body fluid, select bacteria or virus or select protein material or chemicals, may be effected by controlling the scanning radiation per se concentrated on the select matter detected, such as by diverting or levitating same or by increasing the intensity thereof, selectively changing (e.g.— continuously or step increasing the frequency and/or wavelength thereof), an auxiliary beam of radiation may be controllably generated and directed at the select matter as a result of the computer analysis of the laser radiation scanned across the select matter.

OBJECTS OF THE INVENTION

Accordingly it is a primary object of this invention to provide a new and improved system and method for scanning and detecting or identifying select matter of a portion of matter containing such select matter and other matter, in mixture, as cellular tissue or otherwise combined.

Another object is to provide automatic means for detecting and indicating the presence of a select chemical and/or biological material, in a sample of matter or in tissue or body fluid of a living being.

Another object is to provide a system and method for automatically separating select elements of matter from a mixture or culture thereof with other matter.

Another object is to provide a system and method for automatically separating select cells, bacteria, viruses, proteins and the like from body fluid such as blood, lymph fluid, urine, saliva or the like.

Another other is to provide a system and method for genetically altering biological material with radiation.

Another object is to provide a method for automatically scanning and genetically altering or engineering select biological material existing in a mixture thereof or in a liquid, using scanning radiation to detect same.

Another other is to provide a method for automatically scanning and genetically altering or engineering select biological material existing in a mixture thereof or in a liquid, using radiation such as a laser beam to scan and react on same.

Another object is to provide a system and method for selectively combining or fusing select cells of a quantity or mixture of cells together to form interconnected cells or tissue using scanning radiation and the detection of reflections and/or fluorescence radiation resulting from such scanning to control the process.

Another object is to provide a system and method employing one or more scanning radiation beams and one or more detectors of reflected radiation thereof and fluorescent radiation generated when such scanning radiation intersects select matter.

Another object is to provide a system and method for analyzing select matter in a field or sample of such matter by either one of or a combination of computerized image analysis of the matter in the field and computerized fluorescence analysis of select amounts of matter in the field scanned.

Another object is to provide a system and method for analyzing select matter in a field or sample of such matter by a combination of computerized image analysis of the matter in the field and computerized fluorescence analysis of select amounts of matter in the field scanned wherein both scannings occur simultaneously.

Another object is to provide a system and method for analyzing select matter in a field or sample of such matter by a combination of computerized image analysis of the matter in the field and computerized fluorescence analysis of select amounts of matter in the field scanned wherein both scannings occur sequentially.

Another object is to provide a system and method for analyzing select matter in a field or sample of such matter by a combination of computerized image analysis of the matter in the field and computerized fluorescence analysis of select amounts of matter in the field scanned wherein separate beams of radiation are employed to effect each of the scannings.

Another object is to chemically and/or physically alter or etch semi-solid and solid matter using laser techniques.

DETAILED DESCRIPTION OF THE INVENTION AND PREFERRED EMBODIMENTS THEREOF

Figure 1:
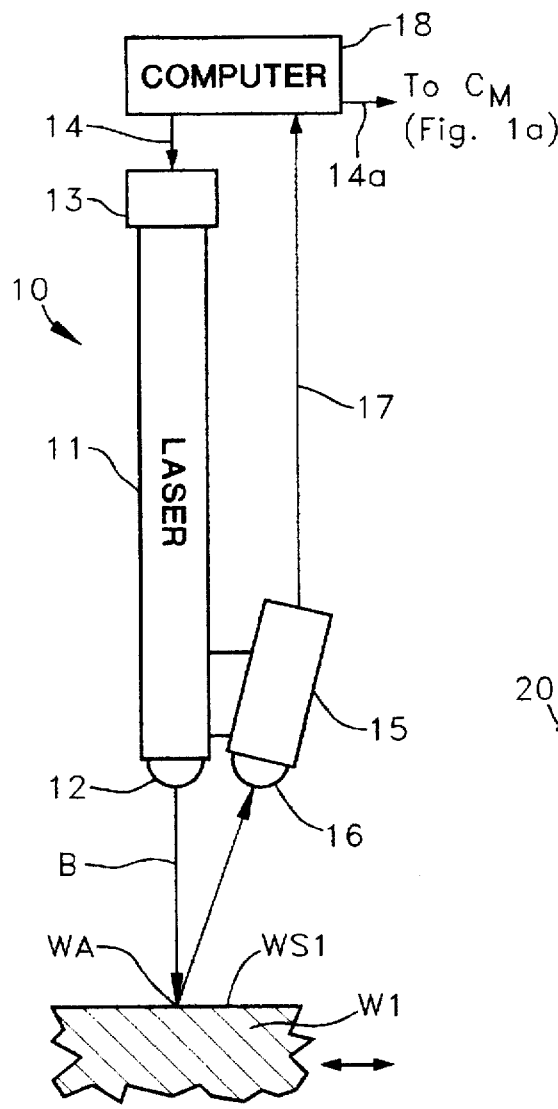
FIGS. 1, 2, 3 and 4 are schematic drawings showing various embodiments for laser beam generation, deflection and sensing.

FIG. 1 shows a portion of an automatic scanning system 10 operable to scan, identify, quantize and/or locate select matter over a scanning field which may be composed of different types of matter such as different molecules, chemicals, cells or a combination thereof and/or other biological matter.

In a preferred form of the invention, automatic computerized scanning of biological matter, tissue, cells, blood or other fluid is performed to detect select biological material over the field scanned, which may contain one or more cancer cells, select proteins or other matter, as well as chemical constituents such as elements, compounds, etc.

FIG. 1 shows a laser 11 operable to generate a laser beam B at output 12 and direct the beam to impinge upon a select area WA of a surface WS1 of a substrate W1 which may define a solid material, a coating, a liquid or a liquid containing solids. The substrate or liquid W1 may be moved along a conveyor, through a duct or conduit or carried in one or more directions such as indicated by arrow A and perpendicular to the plane of FIG. 1, by a manipulator or machine, past laser 11. Laser 11 may also include a mirror M (see FIG. 1a), prism or lens which is controllably deflected or pivoted about a pivot P to cause beam B to scan a select path such as a line, raster, spiral or other path across the surface WS1 while the substrate is stationary or in movement. Mirror M (or a prism or lens—not shown) may also be synchronously pivoted in mutually perpendicular directions about mutually perpendicular or otherwise extending axes. To perform a scan, the sample may be indexed in one (X) direction and the mirror may scan in a mutually perpendicular (Y) or other direction. The specimen may be mounted on a stage.

A computer 18 generates and applies control signals or codes to a controller 13 for operating laser 11, which signals may be in the form of a code or a series of codes operable to variably control the duration, timing, intensity and in certain applications, the wavelength or frequency of the radiation defining beam B in accordance with a scanning program or cycle and/or with feedback signals applied to the control computer 18 and derived from the output of a sensor, such as a photoelectric detector 15, disposed or supported adjacent laser 11 and operable to detect radiation defined by reflections of the radiation of beam B, reflections thereof less absorbed radiation and/or fluorescent radiation caused when the matter intersected by the beam is excited thereby to fluoresce. Detection may be performed by a sensor or sensors responsive to intensity, wavelength, or frequency of the electro-optically sensed radiation. Reflected beams or fluorescent radiation from the specimen may be examined wherein the sensor 15 is part of an electronic spectrometer.

The input 16 to the photoelectric detector 15 may include a deflectable or pivotable mirror which is motor operated to permit the receipt of reflected and/or fluorescent radiation generated by the beam B and intersecting the surface WA and/or matter therebelow.

Figure 1A:
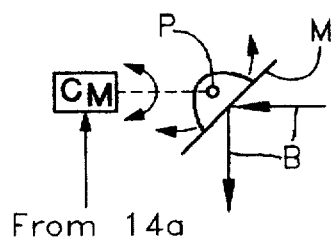
FIG. 1a is a simplified schematic drawing showing a mirror deflection technique for use in the embodiment of FIG. 1.

In the embodiment of FIG. 1a, computer 18 is capable of generating control signals 14a for operating the control motor $C_M$ for pivoting mirror M shown in FIG. 1a. Two such motors are provided to rotate mirror M in mutually different or perpendicular directions.

Figure 2:
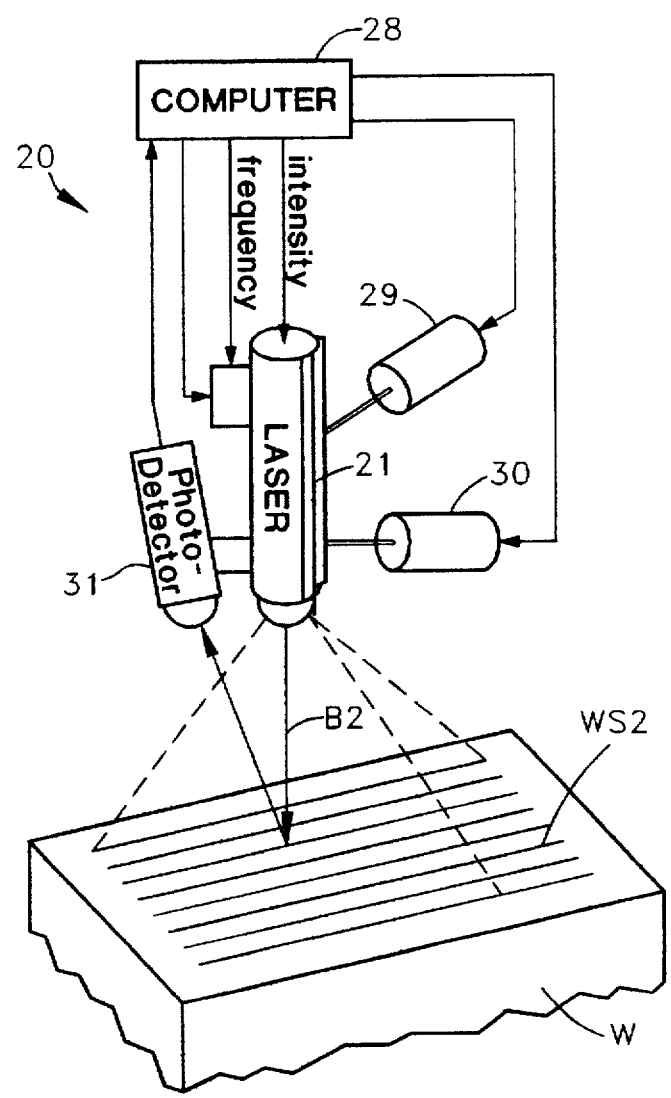

In FIG. 2 is shown a scanning system 10 operable to scan a select path, such as defined by a raster scan (or a spiral scan, if desired), across a surface WS2 of a specimen, skin, tissue, or object W2 or a volume defined by a closed (transparent) container or open container or chamber, to automatically detect (select) variations therein, such as variations in the composition of matter such as molecules, chemicals, biochemicals and/or other biological matter which may vary across the surface scanned and/or in the volume scanned, to quantize and/or locate select variations in or select portions of such matter. Laser 21 is operable to generate an output beam B2 under the control of computer 28 wherein signals from the computer cause the beam to perform a raster scan or other type scan over a select surface portion or volume of a scan field. Such field scanning may be effected one or more times by computer controlling two motors 29 and 30 to control and effect the X and Y directional deflection of a mirror (see FIG. 1a) or other optical device, such as a prism, operable to receive the laser generated beam B2 and direct the beam along a select scanning path across the surface WS2.

In a preferred form, computer 28 is operable to generate control signals, such as codes provided at a plurality of outputs to control the operation of the laser 21 and the beam or mirror deflection devices 29 and 30 (which may be motors or force transducers such as piezo-electric devices) which operate in synchronism to deflect the beam B2. Beam B2 may be operated in an on-off mode (i.e. pulsed), at a fixed frequency or may be varied in frequency (or wavelength) in accordance with the computer program or feedback signals fed to the computer 28 from one or more sensors such as spectrometers, photoelectric cells or photodetectors 31 and/or one or more computers analyzing the signals generated thereby in sensing select radiation generated or caused by the beam B2 as it scans. The reflected beam or fluorescent radiation derived from the specimen may be examined in a variety of ways including computer analysis of signals indicative of wavelength and/or intensity, angle of reflection or fluorescence, etc. generated by the use of appropriate sensors.

Figure 3A:
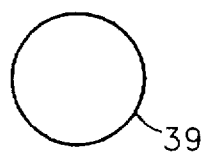
FIGS. 3a and 3b show end views of devices for use in the embodiment of FIG. 3.
Figure 3B:
Figure 3:
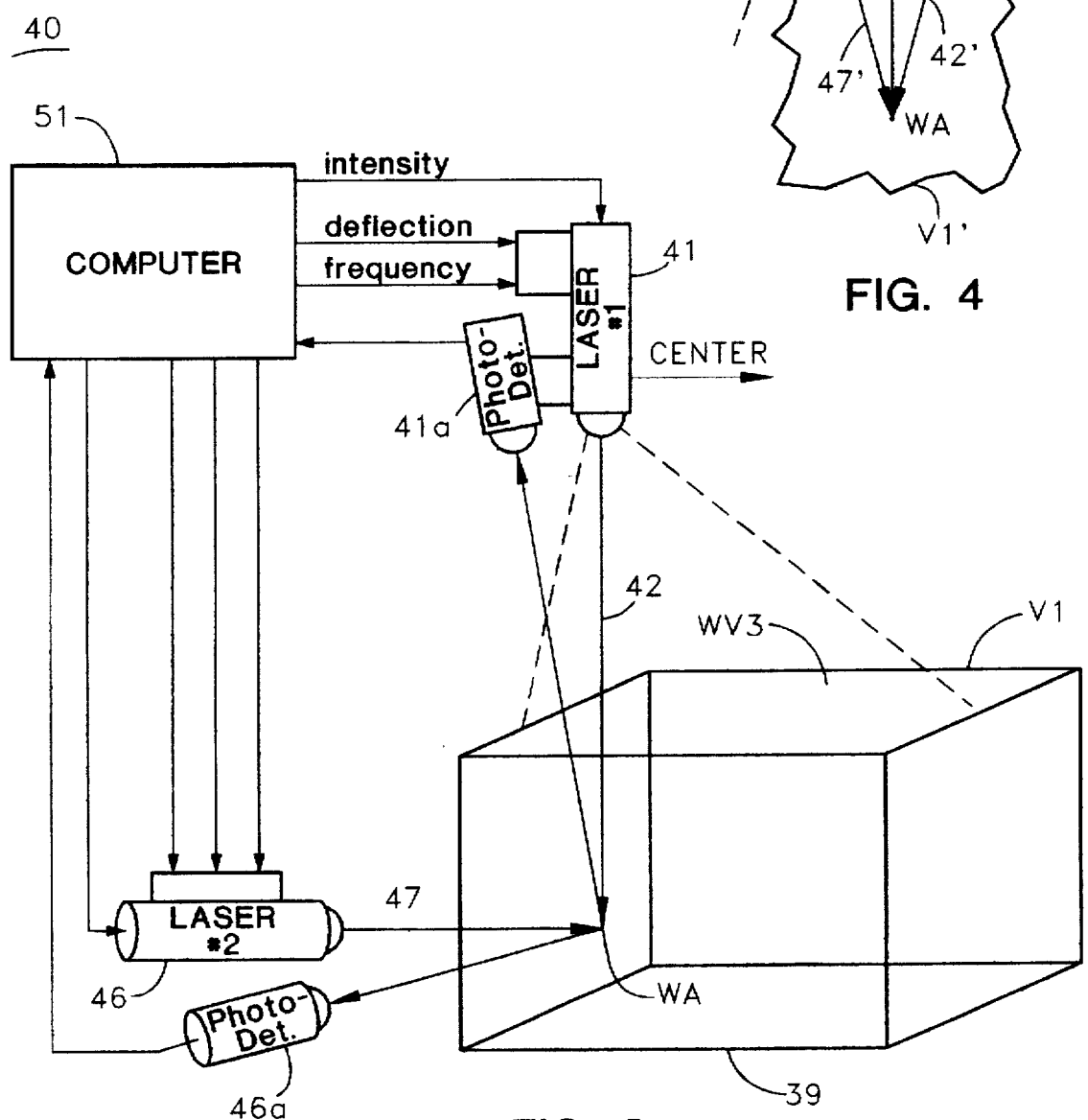

FIG. 3 shows a scanning system 40 operable to scan and detect select matter, cells, molecules or the like in a volume V, such as the interior of a container or duct 39 which may be tubular in shape or may be open at the top (see FIGS. 3a and 3b) or an ambient volume such as a portion of the atmosphere. Two lasers 41 and 46 are arranged on a suitable support (not shown for purposes of simplicity) and spaced apart from and arranged transverse to each other, and have respective outputs 42 and 47, each of which contain a multi-direction (X, Y) or (X, Y, Z) deflection control system for each of the laser beams generated by lasers 41 and 46. Lasers 41 and 46 are each preferably of the tunable type and each is provided with a respective frequency or wavelength varying input controller respectively denoted 43 and 48 which responds to digital or analog output signals generated by the controller or computer 51. The tunable lasers may, for example, be of the type described in the article "Dye-Laser Alternative Cover the Spectrum" appearing at pages 69–76 in the September 1994 issue of Laser Focus World.

Figure 4:
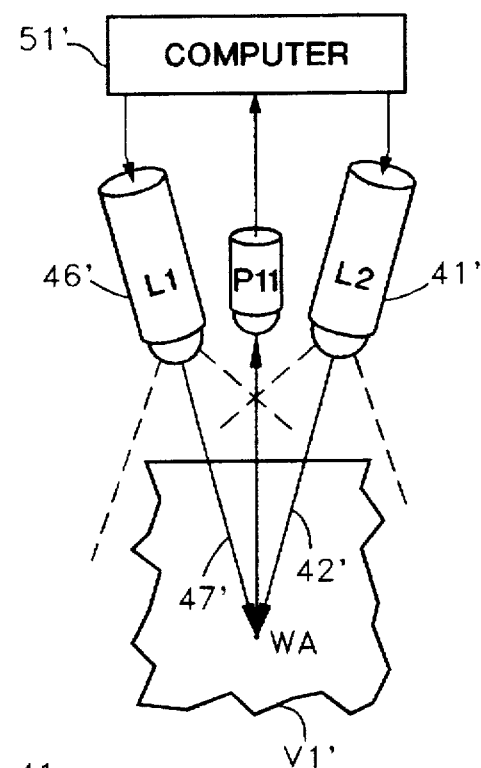

While lasers 41 and 46 are shown supported respectively above and to one side of volume $V_1$ permitting the beams 42 and 47 of each laser to scan and intersect substantially at a right-angle (or greater or less than a right-angle) to each other, lasers 41 and 46 may also be mounted next to each other, as shown by lasers 41' and 46' in FIG. 4, and operable to scan with the beams 42' and 47' thereof intersecting within volume $V_1$ disposed at acute angles to each other as shown.

The lasers 41 and 46 (and 41' and 46') of FIGS. 3 and 4 may be controlled in their operations to automatically scan the fluid, molecules or particles or a fluid containing solid particles in volume $V_1$ (or $V_1'$) along a plurality of layers or stratum therein within which layers the two beams intersect during the scanning of such respective layers so as to impose on the molecules or matter of each layer the combined effect of the two intersecting beams of radiation. By employing this scanning method, matter or molecules in each layer and in the entire volume so scanned by the two beams may be analyzed and/or reacted on by the combined effect of the radiation of the two intersecting beams. In other words, each of the two intersecting beams of radiation may be generated at an intensity (and frequency) such that when they intersect (in volume V), they will generate and direct radiation to matter or molecule(s) at the point or area of intersection which impinging radiation, (i.e. the total of the radiation beams 42 and 47) is sufficient to excite the matter or molecules within such area to fluoresce and/or to reflect same to the exclusion of other matter or molecules along the path of the respective beams other than at the area of intersection thereof. Thus all or a selected portion(s) of volume $V_1$ (or $V_1'$) may be scanned in a three-dimensional scanning operation in which the total volume scanned is divided into a series of separate sheet-like volumes or slices thereof by (computer) deflection controlling the two beams to intersect as they respectively scan within each sheet-like or layer-like volume. Such intersections of the two beams may define raster-like scans within each sheet-like volume which may be substantially repeated from one sheet-like or layer-like volume to the next (therebelow).

If the scanning beam or beams are each controlled in deflection by digital code signals which define or are proportional to coordinate locations of the beam, or two intersecting beams, in the field or volume scanned, the code signals (and/or timing signals generated from the start of scanning) may be employed to indicate the location of the areas intersected by the two beams when select matter or molecules are detected, if it is required to locate and/or quantize such select matter in the volume ($V_1$) scanned. For example, if the two beams are generated at an intensity and/or wave length or frequency wherein the combined effect of both beams on matter at the location of intersection is such as to cause such matter to become excited to fluorescence to the exclusion of other matter intersected by one beam but not the other, then the scanning intersection of the two beams may be employed to investigate or to excite or change matter at select locations within volume $V_1$ and/or just at those locations where select matter exists.

Where system 40 (FIG. 3) is employed to investigate and intelligibly indicate the presence of select matter or molecules in a given volume containing a liquid or gas, system 40 may be operated to detect select matter, quantize or operate on such matter with radiation or to define what matter it detects and operate on or remove selected matter thereof. In a particular form, the system 40 may be employed to destroy select bacteria, virus or cancer cells in tissue or body fluid such as blood, with the radiation of the intersecting beams. The system 40 may also be employed to record digital data in a solid material by using the radiation of the intersecting beams to chemically and/or physically change matter in the spot-like areas intersected by the two beams, in a pulsed operation and to reproduce select information from such record media 30. Also 3D modelling using radiation curable (by the combined radiation of the intersecting beams) photopolymers may be so effected as described above.

Figure 5:
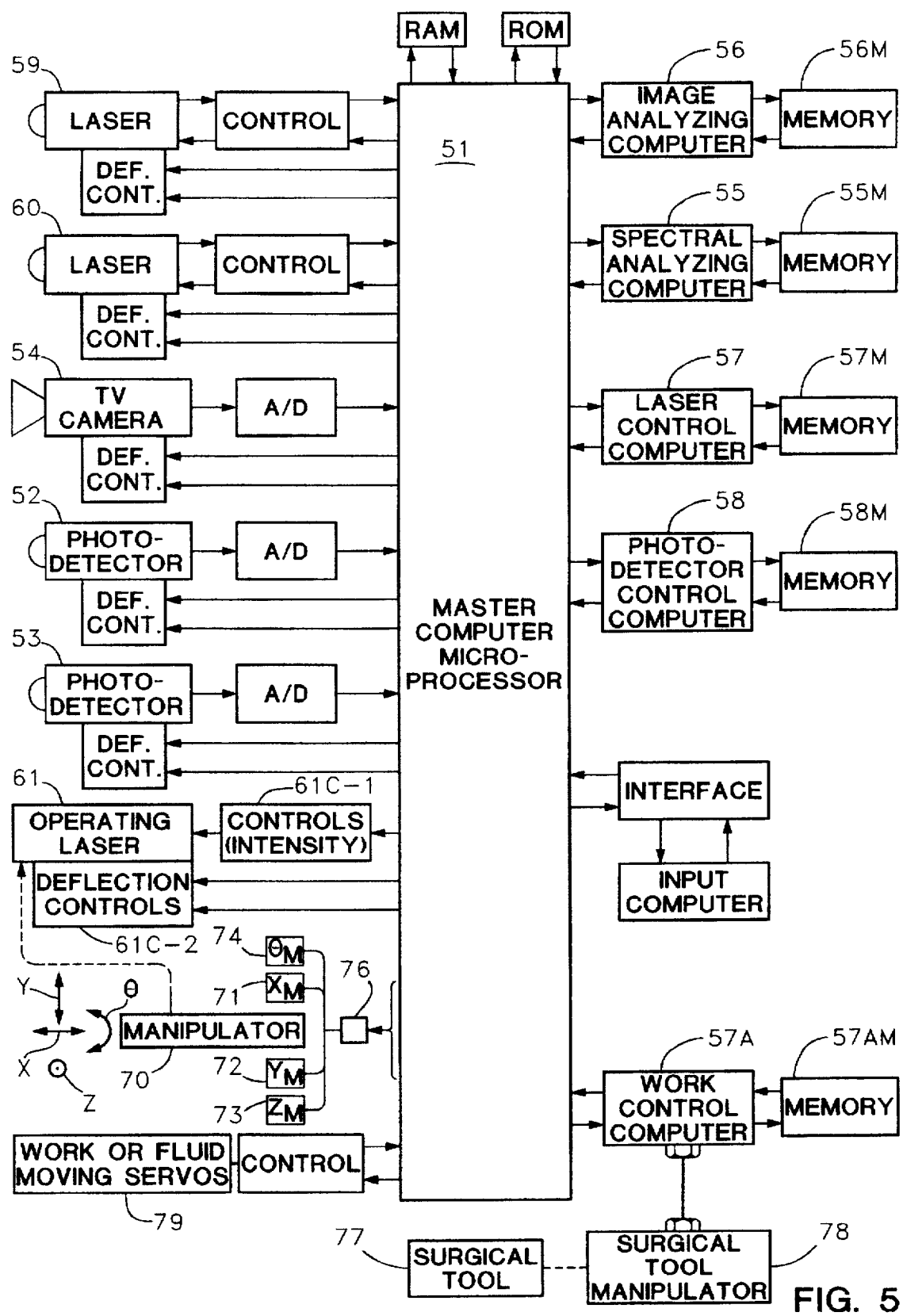
FIGS. 5 and 6 are block diagrams showing different embodiments of computer systems and controls for operating the laser devices shown in FIGS. 1–4.

FIG. 5 is a schematic diagram of a system 50 for automatically controlling the operation of electro-optical scanning apparatus of the types shown in FIGS. 1–4. A master computer or microprocessor 51 synchronizes and controls communications between a television camera 54, one or more electro-optical scanners 52, 53 and spectral and image analyzing computers 55 and 56 respectively, which process and analyze signals generated by the scanners in accordance with information recorded in their memories 55M and 56M and generate respective trains of code signals. Such code signals are passed to a laser control computer 57 and a photodetector control computer 58, each having a respective memory 57M, 58M, and which generate control codes for controlling the operations of the laser 59, 60 and TV 54 scanners and photodetectors 52, 53.

System 50 includes an operating laser 61 and controls 61C-1, 61C-2 therefor which control its operation to cause it to controllably scan and radiate or treat, ablate or destroy select matter such as cancerous tissue detected by the scanners. An automatic manipulator 70 reciprocally movable along directions X, Y, Z and θ is operated by a plurality of reversible gear motors 71–74 and positions and moves treatment laser 61 to permit it to predeterminately operate on select tissue or matter in accordance with command control signals generated by a manipulator control computer 76 which receives and analyzes signals generated by computers 55, 56 through master computer 51. The operating laser 61 may be replaced by one or more powered surgical tools 77 operated under control of a tool manipular 78 and computer 57A in accordance with signals generated by computers 55, 56 and coupled thereto by master computer 51.

Fluids are moved by pumping or by solenoid operating or moving a valve under control of servos 79, control circuits 79A and computer 57 through master computer 51.

Figure 6:
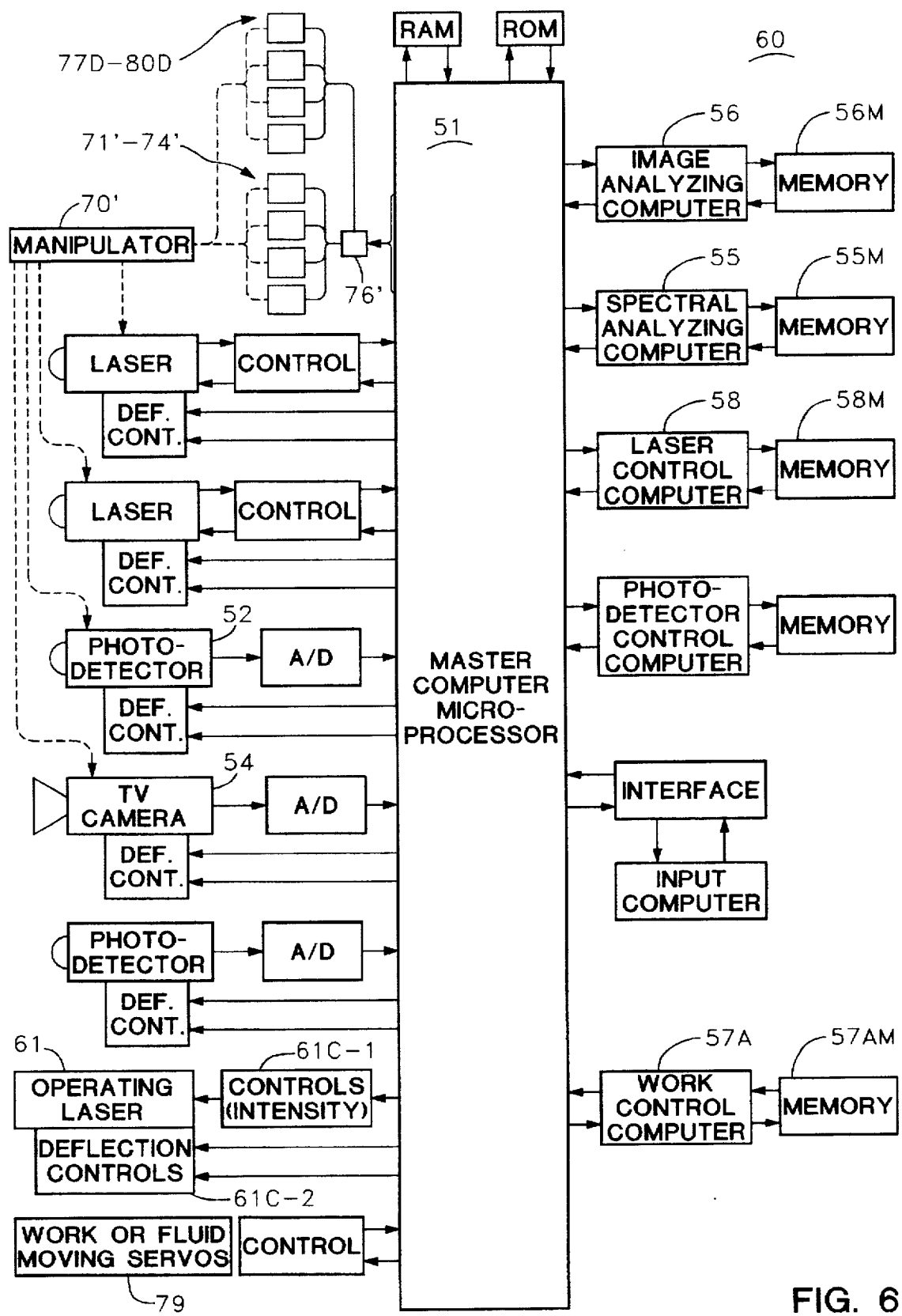

FIG. 6 shows a modified form of the invention defined by a system 60 employing one or more automatic manipulators 70' for positioning the scanning and photoelectric detecting devices and subsystems of FIGS. 1–5 to either preposition same with respect to a living being or object prior to a computer controlled scanning operation and/or to effect an automatic computer controlled electro-optical scanning operation after such prepositioning. The system 60 of FIG. 6 may employ substantially all or some of the devices and subsystems shown in FIG. 5 including one or more lasers supported by one or more manipulator arm assemblies defining or forming part of one or more computer controlled manipulators. The arm assemblies of such manipulator(s) are driven by a plurality of reversible gear motors 71'–74' each containing a respective shaft digitizer 77D to 80D for generating feedback codes which are applied to manipulator control computer 76' for operating the motor(s) in a feedback control mode.

The TV camera 54 may also be supported by the manipulator and is operable to scan its field including the image of the patient or object to be inspected and generates image signals which are digitized and analyzed by image analyzing computer 56 which generates coded control signals in accordance with the information analyzed in that portion of the image field scanned. Such control signals are employed to (a) preposition the manipulator (S) 70, 70', etc. with respect to a select portion of the object or person to be scanned; (b) controllably operate the manipulator and one or more electro-optical scanners such as one or more lasers of the type described, one or more photodetectors, and/or the TV camera 54; (c) controllably operate one or more motors for effecting further scanning operations; and (d) controllably operate one or more motors or devices employed to further operate on the person or object inspected in accordance with the information derived from computer analysis of the image signals derived from such automatic scanning.

Figure 7:
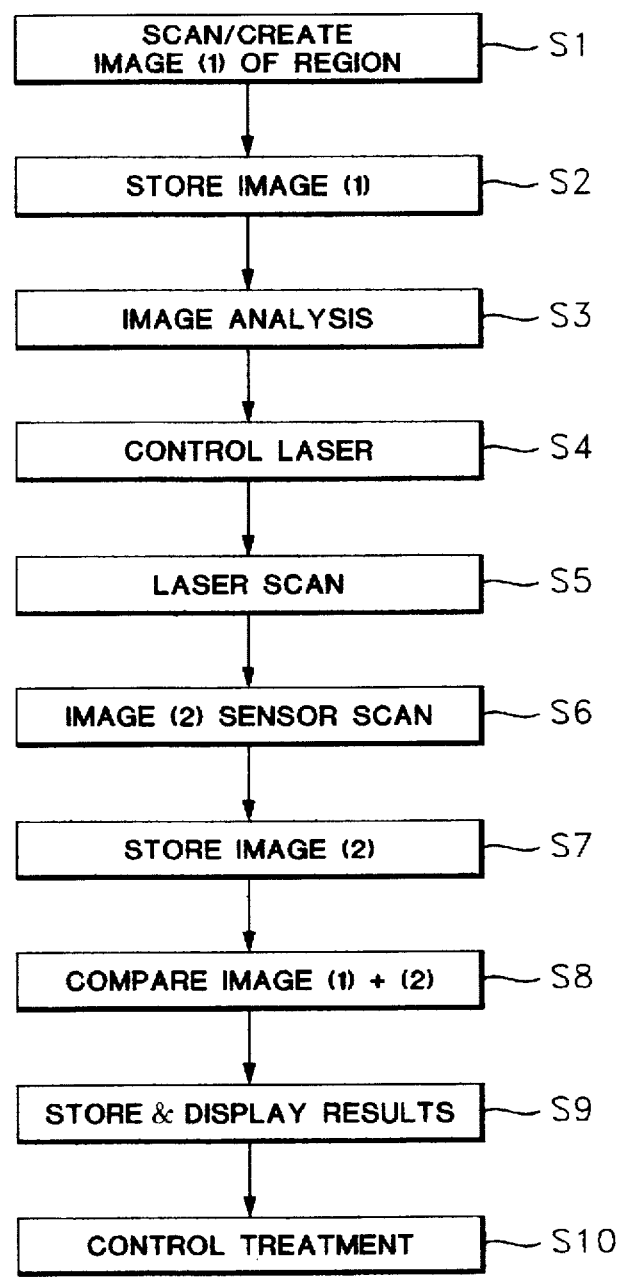
FIG. 7 is a flow diagram showing the manner of computer operation of the various embodiments of the present invention.

FIG. 7 is a flow diagram which is useful in describing the various operations capable of being performed with the apparatus and system of the present invention.

Noting FIG. 7, a cycle is initiated wherein, in method step S1 an image of the region to be analyzed and/or treated is created and, through the use of the TV camera, image signals are generated which image signals are digitized and stored at S2. At S3 the stored image signals are analyzed and a tunable laser is operated at S4 to generate a laser beam of a predetermined: wavelength, frequency, intensity, etc. Also the laser beam wavelength, intensity, frequency, etc. may be varied during scanning or may be controlled to scan different portions of a region at different wavelengths, frequencies or intensities.

At S5, the region is scanned by the beam of laser radiation. At step S6 the signals output by the sensors are examined, and employed to create a second image, the digitized signals of which are likewise stored at S7. At step S8 the first and second image signals are transferred from storage and are compared and analyzed to ascertain information regarding aspects of the examined region such as the presence of a tumor, the stage of a cancer if a cancerous growth is detected, the extent and shape of the malignant region or tumor, etc. At S9 the analyzed information is stored and outputted (i.e. display and/or printout).

In the flow diagram of FIG. 7, the information derived at step S8 may then be used to control and/or direct, at step S10, a beam of laser radiation for treating the malignancy. Alternatively, the operation may be such as to control and manipulate an instrument or a surgical tool to inspect or operate on select tissue (by operating motors, solenoids, valves, or the like).

The control at step S1 may be employed to operate one laser 11 as shown in FIG. 1 or a pair of lasers 41 and 46, as shown in FIG. 3.

The sensors may be the opto-electric device 15 (or devices 41a, 46a of FIG. 3) or a spectrometer or other like instrument.

The sensing operation may examine amplitude or intensity of a reflection or a fluorescence, wavelength or frequency, angle of reflection or radiation.

The control of radiation at step S1 and/or S5 may also include controlling a flow of a fluid (such as blood) when it is a fluid that is being examined, or may control moving a body, a tissue or other matter when such matter is being examined, in addition to laser beam control.

Steps S1 and S5 may further include controlling the interval or intervals that a beam is on.

Timing means is activated as a substep of steps S1 and/or S5 when required to identify a location or locations of a particular condition or site from a given reference or starting point from which a beam originates and then moves to said site.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A method of electro-optically scanning tissue comprising the steps of:
   (a) generating a first beam of radiation;
   (b) scanning said tissue with said first beam of radiation, whereby said beam moves relative to said tissue, to cause said tissue to fluoresce;
   (c) photoelectrically detecting said fluorescence and generating first variable electrical signals at a position to receive both reflected and fluorescent radiation;
   (d) digitizing said first variable electrical signals and generating first digital code signals;
   (e) spectrally analyzing said first digital code signals with a computer and generating second code signals; and
   (f) employing said second code signals to intelligibly indicate the condition of said tissue.

2. The method of claim 1 wherein step (f) further comprises determining if the tissue is diseased.

3. The method of claim 1 wherein step (f) further comprises determining if the tissue is malignant.

4. The method of claim 1 wherein step (f) further comprises determining if the tissue is cancerous or precancerous.

5. The method of claim 1 further comprising the step of generating time code signals during scanning and employing said time code signals to indicate the location of a malignant condition in the first select tissue scan.

6. The method of claim 1 further comprising the step of generating time code signals during scanning and employing said time code signals to indicate the size of a malignant tumor condition in the first select tissue scan.

7. The method of claim 1 further comprising the step of generating time code signals during scanning and employing said time code signals to indicate the size and location of a malignant condition in the first select tissue scan.

8. The method of claim 1 further comprising the step of generating time code signals during scanning and employing said time code signals to indicate the size and location of a plurality of malignant tumor conditions in the first select tissue scan.

9. The method of claim 1 further comprising the step of employing the code signals generated in step (e) to control a process.

10. The method of claim 1 further comprising the step of employing the code signals generated in step (e) to control a machine.

11. The method of claim 1 further comprising the step of employing the code signals generated in step (f) to indicate the presence of a disease.

12. The method of claim 1 further comprising the step of employing the code signals generated in step (f) to indicate a disease wherein said disease is a tumor.

13. The method of claim 1 further comprising the step of employing the code signals generated in step (f) to indicate a disease wherein said disease is a cancer.

14. The method of claim 1 further comprising the step of employing the code signals generated in step (f) to indicate a disease wherein said disease is a cancerous tissue.

15. A method for automatically testing body matter of a living being to determine its contents comprising the steps of:

(a) generating a beam of radiation;

(b) scanning a first amount of body matter with said beam, whereby said beam moves relative to said tissue, to cause said first amount of body matter to fluoresce;

(c) photoelectrically detecting the fluorescent radiation generated by said first amount of body matter at a position to receive both reflected and fluorescent radiation and generating first electrical signals;

(d) computer processing and analyzing said first electrical signals and generating first code signals; and (e) employing said first code signals to intelligibly indicate at least one component of said first amount of body matter.

16. The method of claim 15 wherein said body matter is a body fluid.

17. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, said body fluid being lymph fluid.

18. The method of claim 15 wherein said body matter is blood.

19. The method of claim 15 wherein said method is performed in vivo.

20. The method of claim 15 wherein said method is performed in vitro.

21. The method of claim 15 wherein step (e) further comprises the step of quantizing said component.

22. The method of claim 15 wherein step (e) further comprises the step of quantizing a plurality of select contents of said matter.

23. The method of claim 15 wherein step (a) further comprises generating a beam of laser radiation of a predetermined wavelength.

24. The method of claim 15 wherein step (a) further comprises generating a beam of laser radiation of a predetermined frequency.

25. The method of claim 15 wherein step (a) further comprises:

(f) generating a beam of laser radiation having a wavelength adjusted over a predetermined range.

26. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (d) further comprising operating the computer in an open-loop manner.

27. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (d) further comprising operating the computer in a closed-loop manner.

28. The method of claim 25 wherein step (f) further comprises controllably varying the wavelength of the beam of laser radiation over said predetermined range during a select time interval.

29. The method of claim 25 wherein step (f) further comprises controllably varying the wavelength of the beam of laser radiation over said predetermined range while the beam of laser radiation is scanning tissue.

30. The method of claim 25 wherein step (f) further comprises comprising controllably varying the wavelength of the beam of laser radiation over said predetermined range while the beam is scanning a select location of tissue.

31. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (f) further comprises comprising controllably varying the wavelength of the beam of laser radiation over said predetermined range while the beam is at a select pixel of tissue.

32. The method of claim 25 wherein step (f) further comprises controllably varying the wavelength of the beam of laser radiation over said predetermined range while the laser beam is at a select tumor of the tissue.

33. The method of claim 25 wherein step (f) further comprises controllably varying the wavelength of the beam of laser radiation over said predetermined range while the beam is at a select organ.

34. The method of claim 25 wherein step (f) further comprises controllably varying the wavelength of the beam of laser radiation over said predetermined range while the beam is at a select area of tissue.

35. The method of claim 25 wherein step (f) further comprises controllably varying the wavelength of the beam of laser radiation over said predetermined range during a plurality of select time intervals.

36. A method for automatically testing body matter of a living being to determine its contents comprising the step of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (b) further comprising moving the body matter relative to the beam of radiation.

37. The method of claim 36 wherein the step of moving the body matter further comprises providing a body fluid in motion relative to said radiation beam to effect scanning.

38. The method of claim 15 wherein step (c) further comprises detecting a range of wavelengths of said fluorescent radiation.

39. The method of claim 15 wherein step (c) further comprises detecting a plurality of ranges of wavelengths of said fluorescent radiation.

40. The method of claim 15 wherein step (c) further comprises detecting a range of wavelengths and intensity of said fluorescent radiation.

41. The method of claim 15 wherein step (c) further comprises detecting a range of wavelengths and rate of change of intensity of said fluorescent radiation.

42. The method of claim 15 wherein step (c) further comprises detecting a range of wavelengths and rate of decay of intensity of said fluorescent radiation.

43. The method of claim 15 wherein step (c) further includes analyzing the chemical contents of said body matter.

44. The method of claim 15 wherein step (c) further includes analyzing the biological contents of said body matter.

45. The method of claim 15 wherein said body matter is body tissue.

46. The method of claim 15 wherein said body matter is a body fluid.

47. The method of claim 15 wherein said body matter is blood.

48. The method of claim 15 wherein step (b) further comprises scanning cellular matter.

49. The method of claim 15 wherein step (b) further comprises scanning cells.

50. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (b) further comprising scanning proteins.

51. The method of claim 15 wherein step (a) further comprises providing a tunable laser for generating a beam of laser radiation and tuning said tunable laser to change the wavelength thereof.

52. The method of claim 15 wherein step (a) further comprises providing a tunable laser for generating said beam of laser radiation and controllably tuning said tunable laser to change the frequency thereof.

53. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (b) further comprising impinging the body matter with the beam of radiation whereby fluorescent radiation is generated by the body matter and is modulated with information representing the composition of said body matter.

54. A method for automatically testing body matter of a living being to determine its contents comprising the steps of:

(a) generating a beam of radiation;

(b) scanning a first amount of body matter with said beam to cause said first amount of body matter to fluoresce;

(c) photoelectrically detecting the fluorescent radiation generated by said first amount of body matter and generating first electrical signals;

(d) computer processing and analyzing said first electrical signals and generating first code signals; and (e) employing said first code signals to intelligibly indicate at least one component of said first amount of body matter, step (b) further comprising impinging the body matter with the beam of radiation whereby fluorescent radiation is generated by the body matter and is modulated with information representing the biological composition of said body matter.

55. A method for automatically testing body matter of a living being to determine its contents comprising the steps of:
(a) generating a beam of radiation;
(b) scanning a first amount of body matter with said beam to cause said first amount of body matter to fluoresce;
(c) photoelectrically detecting the fluorescent radiation generated by said first amount of body matter and generating first electrical signals;
(d) computer processing and analyzing said first electrical signals and generating first code signals; and
(e) employing said first code signals to intelligibly indicate at least one component of said first amount of body matter, step (b) further comprising impinging the body matter with the beam of radiation whereby fluorescent radiation is generated by the body matter and is modulated with information representing the chemical composition of said body matter.

56. A method for automatically testing body matter of a living being to determine its contents comprising the steps of:
(a) generating a beam of radiation;
(b) scanning a first amount of body matter with said beam to cause said first amount of body matter to fluoresce;
(c) photoelectrically detecting the fluorescent radiation generated by said first amount of body matter and generating first electrical signals;
(d) computer processing and analyzing said first electrical signals and generating first code signals; and
(e) employing said first code signals to intelligibly indicate at least one component of said first amount of body matter, step (b) further comprising impinging the body matter with the beam of radiation whereby fluorescent radiation is generated by the body matter and is modulated with information to identify the cancerous nature of the body matter.

57. A method for automatically testing body matter of a living being to determine its contents comprising the steps of:
(a) generating a beam of radiation;
(b) scanning a first amount of body matter with said beam to cause said first amount of body matter to fluoresce;
(c) photoelectrically detecting the fluorescent radiation generated by said first amount of body matter and generating first electrical signals;
(d) computer processing and analyzing said first electrical signals and generating first code signals; and
(e) employing said first code signals to intelligibly indicate at least one component of said first amount of body matter, step (b) further comprising impinging the body matter with the beam of radiation whereby fluorescent radiation is generated by the body matter and is modulated with information to identify the non-cancerous nature of the body matter.

58. A method for performing an operation on the body of a living being comprising the steps of:
(a) directing first penetrating radiation against a select portion of a living being, which select portion contains select tissue to be operated on,
(b) after said first radiation has intersected said select tissue and has become modulated with information relating to said select tissue, receiving said radiation with a sensing means and transducing same to electrical signals,
(c) computer processing and analyzing said electrical signals and generating first control signals,
(d) applying said first control signals to control the operation of a power-operated treatment means in a manner to cause said treatment means to perform a first operation on a select portion of said select tissue as determined by the information contained in said first modulated electrical signals, wherein said first operation is operable to effect a first degree of change in said select portion of said select tissue,
(e) thereafter generating and causing an additional amount of said first radiation to penetrate said select tissue and to become modulated in intersecting said select tissue with information defining said select tissue with the change therein effected by said first amount of said treatment radiation,
(f) receiving said additional amount of said first radiation after it is so modulated and transducing same to second electrical signals,
(g) computer processing and analyzing said second electrical signals and generating second control signals,
(h) applying said second control signals to further control the operation of said power operated treatment means to cause it to effect an additional operation on a further select portion of said select tissue.

59. A method in accordance with claim 58 wherein said power operated treatment means comprises a radiation beam generating means and said method further comprises the step of controlling the operation of the radiation beam generating means according to said control signals to selectively irradiate and treat said select portions of said select tissue.

60. A method in accordance with claim 59 wherein said radiation beam treatment means is operated to destroy said select portions of said tissue of said living being.

61. A method in accordance with claim 59 wherein said radiation beam defining said treatment means is operated to change physical characteristics of said select portions of said select tissue.

62. A method in accordance with claim 59 wherein said radiation beam defining said treatment means is operated to change biological characteristics of said select portions of said select tissue.

63. A method in accordance with claim 58 wherein said power operated treatment means comprises a motor driven surgical device and said method further comprises the steps of controlling the surgical device to surgically operate on said select portions of said select tissue under the control of said control signals generated in computer processing and analyzing the electrical signals generated by computer processing and analyzing said electrical signals.

64. A method for operating on tissue deep within a body of a living being comprising the steps of:
(a) providing a high energy radiation beam generating means, such as an ion beam generator preferably generating a beam of particles of sufficient intensity to operate on living tissue,
(b) disposing a living being to be operated on at a select location on a support which is supported adjacent to said beam generating means;
(c) operating said radiation beam generating means in a first mode to generate and direct a beam of charged particles at a select location of the body of said living being and to intersect select body surface tissue of said living being at a select angle thereto and penetrate beneath said body surface tissue by traveling therethrough along a select path.

(d) tuning said radiation beam to a first frequency to cause it to release its particle energy at a select first location within the body of said living being in a manner to irradiate and destroy first tissue at said first location.

65. The method of claim 64 further comprising the step of:

(e) effecting computer-controlled relative movement between said radiation beam and the body of said living being to cause select tissue at the location at which said beam penetrates the living beings body to predeterminately change while simultaneously computer controlling the frequency of said beam in a manner to predeterminately vary same in synchronization with the movement of said beam with respect to the body of said living being whereby the beam intersects and releases its energy within said select tissue adjacent the tissue destroyed by said beam at said first select location.

66. A method in accordance with claim 64 wherein said computer controlled relative movement between said beam and the body of said living being is effected by computer controlling operation of at least one motor operable to variably drive the support for said living being while said living being is immovably retained on said support.

67. A method in accordance with claim 64 wherein said computer controlled relative movement between said beam and the body of said living being is effected by computer controlling the operation of at least one motor operable to selectively control operation of a plurality of motors with each other, which plurality of motors are operable to variably drive the support to said living being in a plurality of directions.

68. A method in accordance with claim 65 wherein said relative movement between the body of said living being and said radiation beam is effected by predeterminately defecting said beam of radiation at a fixed location under computer control in synchronization with the computer controlled variation in the frequency of said beam.

69. A method for treating a malignant growth in a living being comprising the steps of:

(a) initially scanning a select portion of the body containing the malignancy;

(b) generating scanning signals representative of an image of the scanned region which represent radiation which is either reflected or fluoresced from the scanned region;

(c) analyzing the signals representing the image;

(d) scanning said region a second time with a beam of laser radiation by computer controlling a tunable laser to vary one of frequency and wavelength of the beam of laser radiation during scanning;

(e) detecting the radiation fluorescing from the region due to scanning by said beam of laser radiation; and (f) computer analyzing the variable spectral signals to determine the nature of the malignancy.

70. The method of claim 69 wherein the analyzing step further comprises determining one of the type of malignancy, the stage of the malignancy, quantitative data relating to the malignancy.

71. The method of claim 70 wherein the data obtained in the step of determining characteristics of the malignancy further include operating a treatment apparatus.

72. The method of claim 71 wherein the treatment apparatus further includes delivering a drug to the region to be treated.

73. The method of claim 71 further comprising the step of generating a laser beam for treating the malignancy.

74. The method of claim 69 further comprising the step of operating a surgical instrument to treat the malignancy responsive to step (f).

75. The method of claim 15 wherein step (a) further comprises the step of generating said beam of laser radiation of a predetermined intensity.

76. The method of claim 15 wherein step (a) further comprises the step of generating said beam of laser radiation of a first predetermined frequency to scan a first region and of a second predetermined frequency to scan a second region.

77. The method of claim 15 wherein step (a) further comprises the step of:

(f) generating said beam of laser radiation having a wavelength adjusted over a predetermined intensity.

78. The method of claim 15 wherein step (a) further comprises the step of generating said beam of laser radiation of a first predetermined intensity to scan a first region and of a second predetermined intensity to scan a second region.

79. The method of claim 15 wherein step (a) further comprises the step of generating said beam of laser radiation of a first predetermined wavelength to scan a first region and of a second predetermined wavelength to scan a second region.

80. A method of electro-optically scanning tissue comprising the steps of:

(a) generating a first beam of radiation;

(b) scanning said tissue with said first beam of radiation to cause said tissue to fluoresce;

(c) photoelectrically detecting said fluorescence and generating first variable electrical signals;

(d) digitizing said first variable electrical signals and generating first digital code signals;

(e) spectrally analyzing said first digital code signals with a computer and generating second code signals; and (f) employing said second code signals to intelligibly indicate the condition of said tissue;

step (b) further comprising performing a raster scan.

81. A method of electro-optically scanning tissue comprising the steps of:

(a) generating a first beam of radiation;

(b) scanning said tissue with said first beam of radiation to cause said tissue to fluoresce;

(c) photoelectrically detecting said fluorescence and generating first variable electrical signals;

(d) digitizing said first variable electrical signals and generating first digital code signals;

(e) spectrally analyzing said first digital code signals with a computer and generating second code signals;

(f) employing said second code signals to intelligibly indicate the condition of said tissue;

and step (b) further comprises performing a spiral scan.

82. A method for treating living matter comprising the steps of:

generating a beam of radiation;

selecting at least one of the intensity, wavelength, frequency of the beam according to information indicating a given condition of said living matter; and scanning a portion of said matter according to information indicating a location of said given condition.

83. A method of scanning and treating tissue comprising the steps of:

A method of electro-optically scanning tissue comprising the steps of:

(a) generating a first beam of radiation;

(b) scanning said tissue with said first beam of radiation to cause said tissue to fluoresce;

(c) photoelectrically detecting said fluorescence and generating first variable electrical signals;

(d) digitizing said first variable electrical signals and generating first digital code signals;

(e) spectrally analyzing said first digital code signal with a computer and generating second code signals; and (f) employing said second code signals to intelligibly indicate the condition of said tissue;

(g) directing first penetrating radiation against a select portion of a living being, which select portion contains select tissue to be operated on, (h) after said first radiation has intersected said select tissue and has become modulated with information relating to said select tissue, receiving said radiation with a sensing means and transducing same to electrical signals, (i) computer processing and analyzing said electrical signals and generating first control signals, (j) applying said first control signals to control the operation of a power-operated treatment means in a manner to cause said treatment means to perform a first operation on a select portion of said select tissue as determined by the information contained in said first modulated electrical signals, wherein said first operation is operable to effect a first degree of change in said select portion of said select tissue, (k) thereafter generating and causing an additional amount of said first radiation to penetrate said select tissue and to become modulated in intersecting said select tissue with information defining said select tissue with the change therein effected by said first amount of said treatment radiation, (l) receiving said additional amount of said first radiation after it is so modulated and transducing same to second electrical signals, (m) computer processing and analyzing said second electrical signals and generating second control signals, (n) applying said second control signals to further control the operation of said power operated treatment means to cause it to effect an additional operation on a further select portion of said select tissue.

\* \* \* \* \*

UNITED STATES PATENT AND TRADEMARK OFFICE
CERTIFICATE OF CORRECTION

PATENT NO. : 5,735,276
DATED : April 7, 1998
INVENTOR(S) : Jerome Lemelson

It is certified that error appears in the above-identified patent and that said Letters Patent is hereby corrected as shown below:

Column 13, line 29, delete "step" and insert --steps--.

Signed and Sealed this

Sixteenth Day of November, 1999

*Attest:*

Q. TODD DICKINSON

*Attesting Officer*     *Acting Commissioner of Patents and Trademarks*